United States Patent
Balslev

(10) Patent No.: US 11,805,376 B2
(45) Date of Patent: Oct. 31, 2023

(54) HEARING DEVICE COMPRISING AN AUTOMATIC POWER SWITCHING

(71) Applicant: Oticon Medical A/S, Smørum (DK)

(72) Inventor: Jens T. Balslev, Smørum (DK)

(73) Assignee: Oticon Medical A/S, Smørum (DK)

(\*) Notice: Subject to any disclaimer, the term of this patent is extended or adjusted under 35 U.S.C. 154(b) by 219 days.

(21) Appl. No.: 16/907,802

(22) Filed: Jun. 22, 2020

(65) Prior Publication Data

US 2020/0322740 A1 Oct. 8, 2020

Related U.S. Application Data

(62) Division of application No. 15/726,829, filed on Oct. 6, 2017, now Pat. No. 10,779,096.

(30) Foreign Application Priority Data

Oct. 10, 2016 (EP) .................................... 16193091

(51) Int. Cl.
*H04R 25/00* (2006.01)
*A61N 1/36* (2006.01)
(Continued)

(52) U.S. Cl.
CPC ....... *H04R 25/606* (2013.01); *A61N 1/36038* (2017.08); *H02J 50/10* (2016.02); *H02J 50/80* (2016.02); *H02J 50/90* (2016.02); *H04R 25/30* (2013.01); *H04R 25/305* (2013.01); *H04R 25/505* (2013.01); *H04R 25/554* (2013.01); *H04R 25/558* (2013.01);
(Continued)

(58) Field of Classification Search
None
See application file for complete search history.

(56) References Cited

U.S. PATENT DOCUMENTS 6,751,334 B2 6/2004 Håkansson
7,670,278 B2 3/2010 Westerkull
(Continued)

FOREIGN PATENT DOCUMENTS

CN 101400014 A 4/2009
CN 104584587 A 4/2015
(Continued)

*Primary Examiner* — Kaylee R Wilson
(74) *Attorney, Agent, or Firm* — Birch, Stewart, Kolasch & Birch, LLP

(57) ABSTRACT

According to an aspect, a hearing device such as a bone conduction hearing aid is disclosed. The device includes an implantable prosthetic system comprising a receiver coil, and an external audio processor device. The audio processor device includes a microphone configured to transform a received sound into an electrical input signal, a signal processor configured to process the electrical input signal into a processed electrical data signal, a transmitter coil configured to inductively transmit data signals and/or power, across the skin of a hearing device user, to the receiver coil. The audio processor device further includes a detection device configured to detect if the external audio processor device is within a predefined distance from the implantable prosthetic system or to detect if a coupling coefficient between the transmitter coil and a receiver coil is within a predefined value range.

12 Claims, 4 Drawing Sheets

(51) Int. Cl.
*H02J 50/90* (2016.01)
*H02J 50/10* (2016.01)
*H02J 50/80* (2016.01)
*H04B 5/00* (2006.01)

(52) U.S. Cl.
CPC .......... *H04B 5/0031* (2013.01); *H04B 5/0037* (2013.01); *H04B 5/0081* (2013.01); *H04R 2225/61* (2013.01); *H04R 2460/03* (2013.01); *H04R 2460/13* (2013.01)

(56) References Cited

U.S. PATENT DOCUMENTS

| | | |
|---|---|---|
| 8,798,300 B2 | 8/2014 | Jinton |
| 2009/0087005 A1 | 4/2009 | Reithinger |
| 2013/0148828 A1 | 6/2013 | Fort et al. |
| 2014/0056452 A1 | 2/2014 | Moss et al. |
| 2014/0084701 A1* | 3/2014 | Bae .................... H01F 38/14 307/104 |
| 2017/0318399 A1* | 11/2017 | Meskens ............. H04R 25/606 |

FOREIGN PATENT DOCUMENTS

| | | |
|---|---|---|
| WO | WO 02/05590 A1 | 1/2002 |
| WO | WO 2014/031279 A1 | 2/2014 |

* cited by examiner

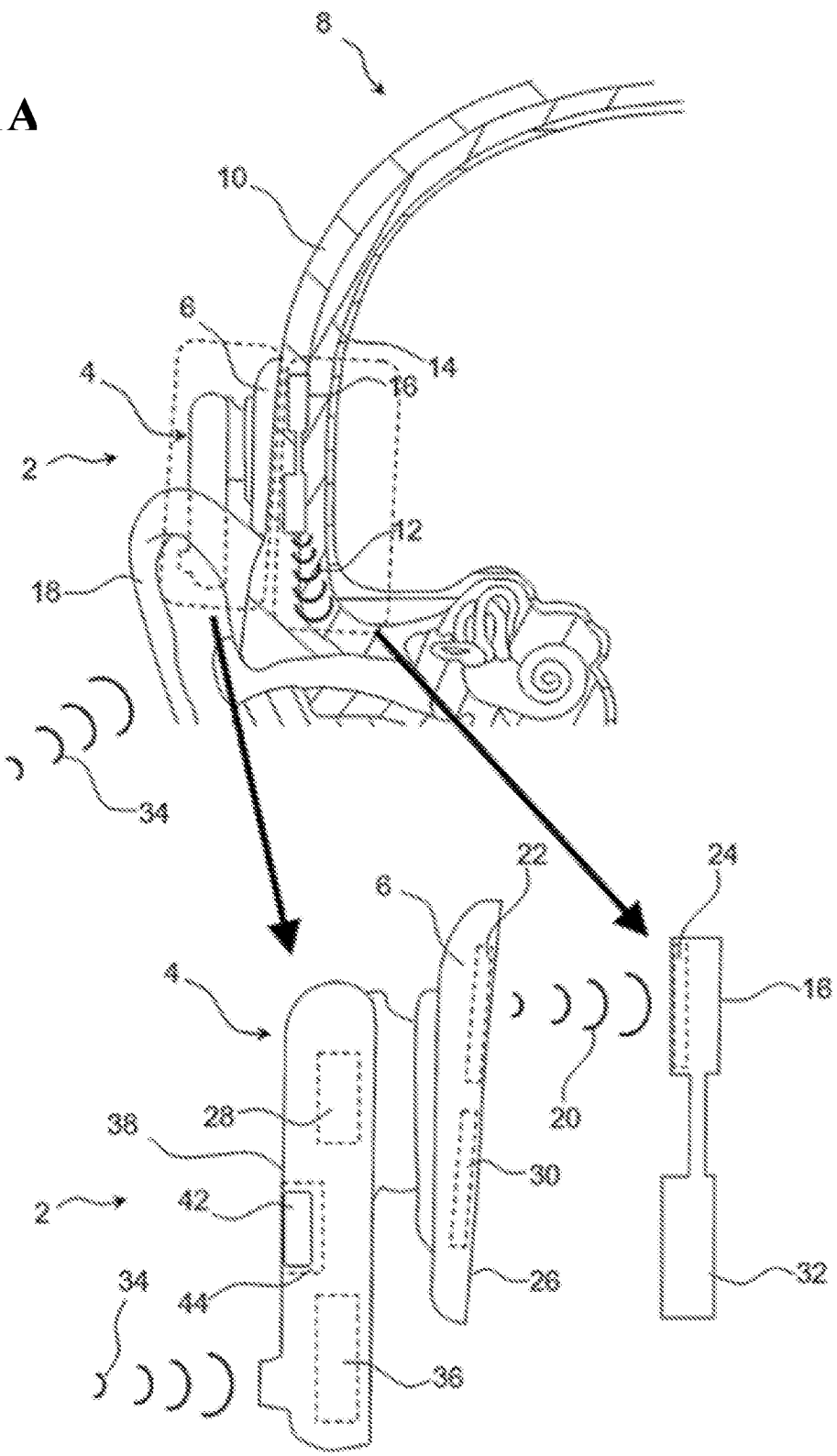

HEARING DEVICE COMPRISING AN AUTOMATIC POWER SWITCHING

CROSS-REFERENCE TO RELATED APPLICATIONS

This application is a Divisional of co-pending application Ser. No. 15/726,829, filed on Oct. 6, 2017, which claims priority under 35 U.S.C. § 119(a) to Application No. 16193091.2, filed in Europe on Oct. 10, 2016, all of which are hereby expressly incorporated by reference into the present application.

FIELD

The present disclosure relates to a hearing device such as an implantable transcutaneous bone conduction hearing aid comprising an implantable prosthetic system. More particularly, the disclosure relates to a bone conduction hearing aid comprising an implantable prosthetic system and being configured to receive its operating energy from an external power source using a radio frequency link.

BACKGROUND

The medical device industry produces a wide variety of electronic and mechanical devices for treating patient medical conditions. Depending upon the medical condition, medical devices may be surgically implanted or connected externally to the patient receiving treatment.

Implantable medical devices are commonly used today to treat patients suffering from various ailments. One type of implantable medical device is a bone conduction hearing aid. A bone conduction hearing aid works by converting the sound signal into a mechanical vibratory stimulus. Heretofore, the vibrating portion of the aid (vibrator) transmits its vibrations to the bone structure of the skull. The vibration of the skull stimulates the cochlea and a sound is perceived.

There are generally five major types of bone conduction devices, including: (1) External bone conduction devices where a vibrator is held to the side of the head by a band that traverses around the head (2) Bone anchored hearing devices where a screw is placed through the skin into the skull and a vibrator transducer is hung to the side of the screw (abutment) (3) Magnetic bone conduction hearing implants, where magnets are implanted and attached to the skull and externally positioned magnets provide a normal force to the side of the head to hold the vibrator to the head; (4) Teeth vibrators where the vibrator is attached to a tooth or a dental implant (5) Active implantable bone conduction devices, where a transducer is implanted under the skin to vibrate the skull.

Some of these bone conduction hearing aids may be partially implantable where a power source is worn outside the patient's body whereas the vibrator is implanted subcutaneously, such as in the type 5 recited in the preceding paragraph. This system requires an antenna to be placed on the patient's skin over the site of an implanted receiver to provide energy and control to the implanted device. Such type of hearing aids receive their operating energy from an external power source like batteries using a radio frequency link, typically to avoid need for implanted batteries. The received energy is then utilized to drive a vibrator that is implanted within the patient. Typical transcutaneous bone conduction hearing aids of today, however, use a high amount of battery power due to the energy demanding transcutaneous link that comprises an external processor with a radio transmitter configured to send a radio frequency magnetic field into the implant in the patient's head via a set of coils.

Since this energy demanding transmission is required to be continuously running in order to enable the hearing aid user to hear, it would be desirable to have a less energy consuming bone conduction hearing aid that includes an implantable prosthetic system and is configured to receive its operating energy from an external power source using a radio frequency link. That is, it would be advantageous to have an efficient energy utilization mechanism, i.e. solution that allows transmission of energy only when there is a need for the operation of such implanted medical devices like in an implanted transcutaneous bone conduction hearing aid.

Because, in known systems, the continued operation of the external signal processor during times of low energy requirement unnecessarily drains the power source such as battery, thereby potentially depleting power source. Therefore, there is a need to overcome the above disadvantage. The present disclosure provides at least an alternative to the prior art bone conduction hearing aids.

SUMMARY

According to an aspect, a hearing device such as a bone conduction hearing aid is disclosed. The hearing device includes an implantable prosthetic system and an external audio processor device. The implantable prosthetic system includes a receiver coil. The external audio processor device may include a microphone configured to transform a received sound into an electrical input signal. The external audio processor device may further include a signal processor configured to process the electrical input signal into a processed electrical data signal. The external audio processor device may further include a transmitter coil configured to inductively transmit data signals and/or power, across the skin of a hearing device user, to the receiver coil of the implantable prosthetic system. The hearing device may further include a detection device configured to detect if the external audio processor device or transmitter coil is within a predefined distance from the implantable prosthetic system or to detect if a coupling coefficient between the transmitter coil and a receiver coil is within a predefined value range.

The detection device may further be configured to detect if the transmitter coil is within a predefined distance from the implantable prosthetic system or to detect if a coupling coefficient between the transmitter coil and a receiver coil is within a predefined value range.

The transmitter coil is adapted to be external to the user body whereas the receiver coil is adapted to be implanted within the user. The transmitter coil and receiver coil may be positionable behind the ear of the user. The transmitter coil and the receiver coil may be configured to be operationally coupled to form a wireless transcutaneous link.

The hearing device may include a bone conduction hearing aid and in particular, it may include a transcutaneous bone conduction hearing aid. The hearing device may include an implantable prosthetic system of any suitable type, size and form.

Hereby, it is possible to detect if the external audio processor device is within a predefined distance (in close proximity to) from the implantable prosthetic system or to detect if a coupling coefficient between the transmitter coil and a receiver coil is within a predefined value range. Accordingly, using the hearing device according to the disclosure it is possible to verify when transmission from the transmitter coil is needed and when it can be turned off or turned into a state of lower power consumption i.e. SLEEP mode (e.g. when the user removes the processor from the head).

The hearing device may include the audio processor, power source such as a battery, transmitter coil and the detection device. The hearing device may further include an implantable prosthetic system (implantable part) comprising the receiver coil configured to be operationally connected to an implantable vibrator unit. The implantable prosthetic system may include a processing unit that is configured to receive and process the data and/or power received by the implantable receiver coil over the wireless transcutaneous link to generate a drive signal for the implantable vibrator (vibrator unit). The vibrator unit is configured to provide vibrations to the skull surface in response to the drive signal, i.e. in response to the data signal and/or power received at the receiver coil. The vibrations are transmitted to the ear via the skull bone.

The external audio processor device may include a microphone configured to transform a received sound into an electrical input signal. The processor device may be of any suitable type. Likewise, the microphone may be of any suitable type and form. The microphone may include one or more multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. In an embodiment, the the microphone may be implantable.

The signal processor may be any signal processor configured to process the electrical input signal into a processed electrical data signal. The signal processing unit may include amplifier that is adapted to apply a frequency dependent gain to the input audio signal. The frequency dependent gain is representative of the data that may be transmitted from the transmitter coil to the receiver coil.

The transmitter coil is configured to inductively transmit data signals and/or power, across the skin of a hearing device user, to a receiver coil of the implantable prosthetic system. The transmitter coil may have any suitable type and form.

The detection device is configured to detect if the external audio processor device is within a predefined distance from the implantable prosthetic system or to detect if a coupling coefficient between the transmitter coil and a receiver coil is within a predefined value range. The detection device may comprise any suitable unit such as voltage measuring unit or a current measuring unit configured to detect if the external audio processor device is within a predefined distance from the implantable prosthetic system.

The predefined distance may be any suitable distance e.g. less than 20 mm, less than less than 15 mm, such as less than 11 mm or less than 8 mm or less than 5 mm or less than 3 mm or less than 2 mm. The predetermined distance may be defined as a function of thickness of skin at the implantation site such as over the mastoid region of temporal bone.

The detection device may be configured to detect if the coupling coefficient between the transmitter coil and a receiver coil is a percentage of the maximum coupling coefficient, e.g. 80-90%, 70-80%, 60-70%, 50-60%, 40-50%, 30-40% of the maximum coupling coefficient.

The detection device may further be configured to detect the distance or coupling coefficient between the transmitter coil and the receiver coil. Hereby, it is possible to utilize the detected distance or coupling coefficient between the transmitter coil and the receiver coil to determine when transmission from the transmitter coil is needed and when it can be turned off or switched to a SLEEP mode (e.g. when the user removes the processor from the head). Accordingly, a less energy consuming hearing device can be provided by turning off the transmitter coil when no transmission is needed.

The detection device may be configured to detect the distance between the transmitter coil and the receiver coil by measuring the coupling coefficient between the transmitter coil and the receiver coil. The coupling coefficient may be representatively computed by utilizing the disclosed current measuring circuitry or voltage measuring circuitry.

The processor device may include a determination unit configured to automatically switching operating mode of the external audio processor device:

I) from an ON mode to a SLEEP mode/OFF mode or

II) from a SLEEP mode/OFF mode to an ON mode in accordance with the determined distance or determined coupling coefficient.

Hereby, the determination unit of the processor device is capable of saving energy by automatically switching operating mode of the external audio processor device from an ON mode to a SLEEP mode/OFF mode when the determined distance or determined coupling coefficient indicates that the transmitter coil does not need to be active i.e. in deactivated state (e.g. when the user takes off the external audio processor). Moreover, the determination unit of the processor device is capable of automatically switching operating mode of the external audio processor device from a SLEEP mode/OFF mode to an ON mode in accordance with the determined distance or determined coupling coefficient. Accordingly, the determination unit of the processor device can activate (i.e. activated state) the transmitter coil when needed (e.g. when the user puts on the external audio processor).

The hearing device may be configured to be in SLEEP mode/OFF mode or to be switched into SLEEP mode/OFF mode. The SLEEP mode/OFF mode is an energy saving mode in which the transmitter coil is deactivate, i.e. not transmitting data and/or power. Hereby, electrically power can be saved. Although the transmitter is deactivated in both the SLEEP and OFF mode, but in the OFF mode all electrical components are in switched off mode whereas in the SLEEP mode, other electrical components are in low power mode.

The hearing device may be configured to be in ON mode or to be switched into ON mode. The ON mode is a mode in which the transmitter coil is activate, i.e. transmitting data and/or power.

The detection device may further include a parameter measuring circuitry, which in response to a controlled signal of predefined characteristics applied to the transmitter coil is configured to measure a quantity value associated with the transmitter coil and/or processor device for determining the distance or coupling coefficient between the transmitter coil and the receiver coil. Hereby, the parameter measuring circuitry allows for applying a controlled signal of predefined characteristics to the transmitter coil in order to measure a quantity value associated with the transmitter coil and/or processor device for determining the distance or coupling coefficient between the transmitter coil and the receiver coil.

Accordingly, it is possible to apply a suitable controlled signal of predefined characteristics to the transmitter coil for the purpose of determining the distance or coupling coefficient between the transmitter coil and the receiver coil in an easy and/or effective manner.

The controlled signal may be provided using a battery, which is housed, may be in a battery compartment, within a processor housing. Hereby, the distance or coupling coefficient between the transmitter coil and the receiver coil can be determined in by using technical features already available in standard hearings aids.

The parameter measuring circuitry may include a current measuring circuitry, wherein the controlled signal comprises a current signal, wherein the predefined characteristics comprises a current of predefined magnitude corresponding to a stimulation current level for a specific frequency for the user, and the measured quantity value is the transmitter coil current and/or the processor device current.

The current measuring circuitry of the parameter measuring circuitry may be used to measure if the magnitude of a measured current signal through the transmitter coil corresponds to a stimulation current level for a specific frequency for the user. Accordingly, the hearing device can determine the distance or coupling coefficient between the transmitter coil and the receiver coil in an easy and reliable manner.

The parameter measuring circuitry may include a voltage measuring circuitry, wherein the controlled signal comprises a voltage, wherein the predefined characteristics comprises a voltage generating a current of predefined magnitude corresponding to a stimulation current level for a specific frequency for the user, and the measured quantity value is the voltage across the transmitter coil and/or voltage across the processor device.

In this scenario, the voltage measuring circuitry of the parameter measuring circuitry can be used to measure if the magnitude of a measured voltage signal across the transmitter coil corresponds to a stimulation current level for a specific frequency for the user for a specific frequency for the user. Accordingly, the hearing device can determine the distance or coupling coefficient between the transmitter coil and the receiver coil in an easy and reliable manner.

The detection device may be configured to access a characteristic quantity value stored in a memory, which is housed within the processor housing and the characteristic quantity value being defined in accordance with a frequency curve parameters defining force output of the vibrator as a function of frequency.

Hereby, the detection device is capable of storing and accessing the characteristic quantity value. Accordingly, the characteristic quantity value can be used for a subsequent process such as comparison with a measured quantity value in order to determine the distance or coupling coefficient between the transmitter coil and the receiver coil in an easy and reliable manner.

The detection device may be configured to compare the measured quantity value with the accessed characteristic quantity value. Hereby, the detection device can determine the distance or coupling coefficient between the transmitter coil and the receiver coil by comparing the measured quantity value with the accessed characteristic quantity value.

The detection device may be configured to generate a compared result based on the comparison, representing the determined distance or coupling coefficient between the transmitter coil and a receiver coil.

Hereby, the detection device can be used to determine if the transmitter coil needs to be deactivated (e.g. when the user takes off the hearing device) or needs to be activated (e.g. when the user puts on the hearing device).

The detection device may be configured to instruct the determination unit to, with the transmitter coil and/or external audio processor in the SLEEP/OFF mode, automatically switch the transmitter coil and/or external audio processor from the SLEEP/OFF mode to ON mode if the compared result is within a predefined acceptable variation.

Hereby, the hearing device can automatically be switched from the SLEEP/OFF mode to the ON mode by defining a suitable predefined acceptable variation range. Moreover, the device can be maintained in the SLEEP/OFF mode as long as the compared result is not within (outside) the predefined acceptable variation.

The detection device may be configured to instruct the determination unit to, with the transmitter coil and/or external audio processor in the SLEEP/OFF mode, automatically maintain the transmitter coil and/or external audio processor in the SLEEP/OFF mode if the compared result is outside the predefined acceptable variation.

Hereby, the hearing device can be maintained in the SLEEP/OFF mode as long as the compared result is outside the predefined acceptable variation.

The detection device may be configured to instruct the determination unit to, with the transmitter coil and/or external audio processor in the ON mode, automatically switch the transmitter coil and/or external audio processor from the ON mode to SLEEP/OFF mode if the compared result is outside a predefined acceptable variation.

Accordingly, the hearing device may automatically be switched into an energy saving mode when the transmitter coil is not required to be actively transmitting. Therefore, the determination unit is adapted to prevent transmission. Accordingly, a less energy consuming hearing device can be provided.

The detection device may be configured to instruct the determination unit to, with transmitter coil and/or external audio processor in the ON mode, maintain the transmitter coil and/or external audio processor in the ON mode if the compared result is within a predefined acceptable variation (range).

Hereby, the device can be maintained in the ON mode as long as the compared result is within the predefined acceptable variation (range).

The predefined acceptable variation may correspond to the predefined distance or the predefined value range.

Hereby, the acceptable variation (range) can be used to determine if the predefined distance or coupling coefficient between the transmitter coil and the receiver coil is within the predefined distance range or the predefined value range.

Accordingly, the acceptable variation (range) can be used as a reference for determining if the with transmitter coil and/or external audio processor should be maintained in its mode or be switched into another mode.

During the SLEEP/OFF mode, the determination unit may be configured to deactivate transmission from the transmitter coil for a first predefined time period. Hereby, it is possible to deactivate the transmitter coil in order to reduce the power consumption in a predefined time period. It may be an advantage that the determination unit is configured to activate transmission from the transmitter coil automatically when the first time period has expired.

During the SLEEP/OFF mode, the determination unit may be configured to deactivate transmission from the transmitter coil for a first predefined time period, wherein the determination unit is configured to activate the transmitter coil for a second predefined time period, during which the measured quantity value and comparison result are generated for determining if the external audio processor device is within a predefined distance from the implantable prosthetic system or if a coupling coefficient between the transmitter coil and a receiver coil is within a predefined value range, wherein:

if the compared result is within the predefined acceptable variation, then the determination unit is configured to automatically switch the transmitter coil from the SLEEP/OFF mode to ON mode or if the compared result is outside the predefined acceptable variation, then the determination unit is configured to deactivate and switch back the transmitter coil to the SLEEP/OFF mode.

Hereby, it is possible to:

automatically switch the transmitter coil from the SLEEP/OFF mode to ON if the compared result is within the predefined acceptable variation;

automatically deactivate and switch back the transmitter coil to the SLEEP/OFF mode, if the compared result is outside the predefined acceptable variation.

Accordingly, the hearing device is configured to save power and still ensure that the transmitter coil is activated when needed.

During the ON mode, the determination unit may be configured to during recurrent time periods, generating the measured quantity value and comparison result for determining if the external audio processor device is within a predefined distance from the implantable prosthetic system or if a coupling coefficient between the transmitter coil and a receiver coil is within a predefined value range; wherein if the compared result is within the predefined acceptable variation, then the determination unit is configured to maintain the transmitter coil in the ON mode; or if the compared result is outside the predefined acceptable variation, then the determination unit is configured to deactivate and automatically switch the transmitter coil from ON mode to the SLEEP/OFF mode.

Hereby, it is possible to provide a hearing device that is configured to save power and still ensure that the transmitter coil is activated when needed.

In some situations, such as when the transmitter coil is proximate to a metal plate instead of the receiver coil, the measured current may be within the normal usage range. Therefore, in order to avoid a false positive and automatic switching to ON mode, refinement to the Auto-On may be applied.

The implanted part of the implantable bone conduction hearing aid includes an electromagnetic vibrator, which has known characteristic impedance that varies across the audio frequency range, and a mechanical resonance typically within a 700 Hz-1000 Hz. Such electromagnetic vibrators are known in the art such as in U.S. Pat. Nos. 8,798,300, 6,751,334, which are incorporated herein by reference. Thus across a frequency range, in position of use (coupled transmitter and receiver coil), the characteristic impedance of the vibrator affects the measured transmitter current/voltage across the transmitter coil in a predictable way when a controlled signal of predefined characteristics is applied to the transmitter coil.

Therefore, in an embodiment, when a current measurement or voltage measurement within the normal range is detected, further transmitter current measurements or transmitter voltage measurement at different frequencies may be performed and compared with transmitter current or voltage corresponding to the different frequencies for the transmitter positioned on the head situation. This may be performed by transmitting one or more discrete tones at high frequency modulation or via a frequency sweep.

When the compared result based on the measured quantity value is within the predefined acceptable variation, the parameter measuring circuitry may be configured to measure at least one subsequent quantity value associated with the transmitter coil and/or processor device in response to at least one subsequent controlled signal of at least one subsequent predefined characteristics applied to the transmitter coil.

Hereby, for a vibrator with known characteristic frequency curve, it would be possible to compare the pattern of measured current and the current from the known characteristic curve to determine whether the external audio processor device is close to the implantable prosthetic device or another object. Accordingly, if the condition is satisfied, the external audio processor device returns to normal mode of the operation, else the external audio processor device stays in OFF mode/Sleep mode.

The external audio processor device may be configured to continually goes through a cyclical step of determining whether the implant is nearby.

The detection device may be configured to access at least one characteristic quantity value stored in the memory, which is housed within the processor housing and the at least one characteristic quantity value being defined in accordance with the frequency curve parameters of the hearing device; and generate at least one compared result by comparing the at least one subsequent measure quantity value with corresponding the at least one accessed characteristic quantity value.

Hereby, the hearing device is capable of applying characteristic quantity value stored in the memory.

The determination unit may be configured to automatically switch the transmitter coil and/or external audio processor from the SLEEP/OFF mode to ON mode if the compared result and at least one additional compared result is within the predefined acceptable variation and at least subsequent predefined acceptable variation respectively.

Hereby, it is ensured that hearing device is switched in to the ON mode when required.

The controlled signal and the at least one subsequent controlled signal may include one or more discrete tones at a predefined modulation or a frequency sweep. Hereby, it is possible to let the determination unit apply a predefined reliable and valid methodology comprising a controlled signal and the at least one subsequent controlled signal.

The processor device may include a processor housing provided with a battery arranged in a battery compartment within the processor housing.

No transmission over the wireless transcutaneous link may be accomplished by the transmitter coil during at least a portion of the power saving mode.

The determination unit may be configured to automatically switching the hearing device and hereby the external audio processor device from an ON mode to an OFF mode/Sleep mode. Hereby, electrical power can be saved.

The processor device may include a determination unit configured to automatically switching the hearing device and hereby the external audio processor device from the power saving mode to the ON mode. Hereby, it is ensured that the hearing device can be brought into ON mode when required.

The processor device may include a coupling determination unit configured to determine the coupling coefficient between the transmitter coil and the receiver coil. Hereby, it is possible to apply the coupling coefficient between the transmitter coil and the receiver coil to determine if the hearing device should be switched from one mode into another mode or if the hearing device should be maintained in the same mode.

The current measuring circuitry or voltage measuring circuitry may be configured to measure a mean value of the current or voltage for a predefined time period. Hereby, the mean value of the current or voltage can be used to determine if the hearing device should be switched from one mode into another mode or if the hearing device should be maintained in the same mode.

The current measuring circuitry or voltage measuring circuitry may be configured to measure a mean value of the current or voltage for a predefined time period of at least 10 mS, such as 100 mS or 1 second.

The hearing device may include a user interface member (e.g. a pushbutton or a touch screen or gesture controls) for manually switching the hearing device to the ON mode and/or an OFF mode. Hereby, it is possible to manually control the hearing device.

The processor device may be configured to deactivate transmission from the transmitter coil for a first predefined time period and activate the transmitter coil for a second predefined time period during an OFF mode/Sleep Mode (power saving mode), wherein the detection device is configured to detect if the external audio processor device is within a predefined distance from the implantable prosthetic system during the time periods in which the transmitter coil is activated. Hereby, it is possible to deactivate the hearing device and on a regular basis determine if the hearing device should be turned on.

The processor device may be configured to switch the hearing device and hereby the external audio processor device to an ON mode when the external audio processor device is within a predefined distance from the implantable prosthetic system. Hereby, it is ensured that the hearing device is activated when required.

The predefined distance may correspond to the distance between the external audio processor device and the implantable prosthetic system during normal operation.

The first predefined time period ($T_1$) may be about 0-1 seconds, such as 0.5 seconds and where the second predefined time period ($T_2$) is about 2-10 seconds, such as 3-5 seconds, such as about 3.5 seconds.

The hearing device may include a current measuring circuitry configured to measure additional transmitter coil currents and/or processor device currents when a current measurement is detected falling within a predefined normal range, wherein the additional transmitter coil currents and/or processor device currents are measured by transmitting one or more discrete tones at a predefined frequency modulation or via a frequency sweep.

The processor device may be configured to detect if the measured additional transmitter coil currents and/or processor device currents matches a predefined range of the transmitter current with the hearing device in operational position.

The hearing device may be configured to returns to ON mode if the measured additional transmitter coil currents and/or processor device currents matches the predefined range of the transmitter current with the hearing device in operational position and otherwise stay in OFF mode/Sleep mode (power saving mode).

According to another aspect of the disclosure, the hearing system comprising a hearing device according to the disclosure and an implantable prosthetic system comprising a transducer for generating an output signal.

The transducer may be an implanted vibrator configured to generate mechanical vibrations.

The transducer is a stimulator secured in bone beneath the skin, wherein the stimulator is configured to convert the received signals into electric impulses and send them through an internal cable to an array of electrodes wound through the cochlea. An illustrative implementation is shown in U.S. Pat. No. 7,670,278, which is incorporated herein by reference.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIG. 1A shows a cross-sectional view of a hearing device arranged on a hearing device user;

FIG. 1B shows a close-up view of the hearing device shown in FIG. 1A;

DETAILED DESCRIPTION

Figure 2A:
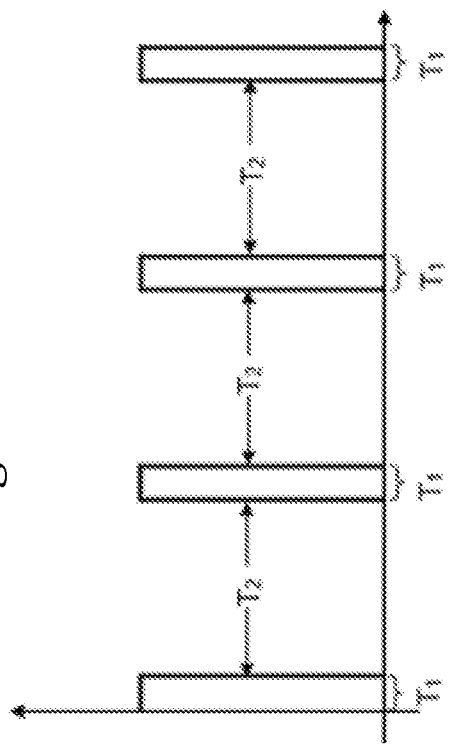
FIG. 2A shows a first graph with two alternating phases.

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device adapted to receive an audio signal electronically, possibly modifying the audio signal and providing the possibly modified audio signals as an audible signal to at least one of the user's ears. Such audible signals may be provided in the form of an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging an external unit of the hearing device behind the ear and positioning it over an implanted unit through magnetic attraction between the external unit and the implanted unit such as in a transcutaneous bone conduction hearing aid.

A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an external input unit such as a microphone for receiving an acoustic signal from a user's surroundings and providing a corresponding electrical input signal, ii) an external signal processor adapted to process the electrical input signal, iii) a transmitter coil adapted to transmit the processed electrical input signal, iv) an implanted receiver coil adapted to receive the processed electrical input signal and power from the transmitter coil, and v) a stimulator unit adapted to receive the processed electrical input signal from the receiver coil and to produce stimulation that is perceived as sound by the hearing aid user.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The stimulator unit may include an output transducer such as a vibrator that converts produces mechanical vibrations such as in bone conduction hearing aid or one or more output electrodes for providing the electric signals such as in a Cochlear Implant.

Now referring to FIG. 1A, which illustrates a hearing device 2 according to an aspect of the disclosure shows a cross-sectional view of a hearing device 2 such as a transcutaneous bone conduction hearing aid arranged on a hearing aid user 8.

The hearing device 2 (surrounded by a dotted line) is a transcutaneous bone anchored hearing device 2 comprising an external audio processor device 4 connected to a coupling member 6. The coupling member 6 of the hearing device 2 is attached to the skin 10 of the hearing device user 8 behind the ear 18 of the hearing device user 8 by means of magnetic attraction between an external magnet (not shown) and an implantable magnet (not shown) of an implantable prosthetic device 16 implanted subcutaneously under the skin 10 into the skull bone 14. The implantable prosthetic device 16 is a small implant (typically made of titanium) that is mounted on the skull bone 14 behind the ear 18. The implantable prosthetic device 16 comprises an implantable magnet (not shown) attached and hidden beneath the skin 10. The external audio processor device 4 of the hearing device 2 is attached to an external magnet (not shown) and the external audio processor device 4 is kept in place by magnetic attraction between the implant magnet and the external magnet (not shown). Sound 34 received by the external audio processor device 4 is processed and along with power is transmitted from the external audio processor device 4 using an external transmitted coil to an implantable receiver coil of the implantable prosthetic device 16. The signal (representative of sound processed by the external audio processor device 16) received at the receiver coil is delivered to an implanted vibrator that produces mechanical vibrations, which are directed through the skull bone 14 to the inner ear for producing sound perception.

FIG. 1B illustrates a close-up view of the hearing device 2 shown in FIG. 1A. It can be seen that the hearing device 2 comprises an external audio processor device 4 having a microphone 36 provided in a housing 38. The external audio processor device 4, moreover, comprises a battery 42 arranged in a battery compartment 44. The external audio processor device 4, additionally, comprises a signal processor 28, The hearing device 2 comprises a coupling member 6 provided with a skin contact surface 26 configured to be brought into contact with the skin 10 of the hearing device user 8 when the hearing device 2 is attached on the hearing device user 8. The coupling member 6 may include a detection device 30 arranged below a transmitter coil 22. The detection device 30 may be arranged within the housing 38.

An implantable prosthetic device 16 is provided next to the hearing device 2. The implantable prosthetic device 16 comprises a receiver coil 24 and a vibrator 32. The vibrator 32 is adapted to be positioned on the outer skull surface or in recess created in the skull bone.

Sound 34 is received by the microphone 36 of the external audio processor device 4. The sound 34 received by the microphone 36 is processed by the signal processor 28 and transmitted to the receiver coil 24 as a signal 20 by the transmitter coil 22. The vibrator 32 of the implantable prosthetic device 16 is configured to generate vibrations that are directed through the skull bone 14 to stimulate the inner ear.

FIG. 2A illustrates a curve showing the activity of the external audio processor device of a hearing device according to an aspect of the disclosure. The activity is plotted against time in on the X-axis and state (ON or OFF/SLEEP) on the Y-axis. $T_1$ represents transmitter in an activated state and $T_2$ represents transmitter in a deactivated state. The external audio processor device is in ON mode (first $T_1$ time period) and once it is determined based on the quantity measurement that the transmitter should be in OFF/SLEEP mode, then following the ON mode, the transmitter is switched to OFF/SLEEP mode for time periods $T_2$. During the OFF/SLEEP mode, the transmitter may be temporarily switched on (as indicated by following $T_1$ time periods), interrupting the OFF/SLEEP period, for measuring the quantity. During the temporarily ON mode, the quantity (e.g. current) of the transmitter coil is measured and compared against the normal (expected) range. If the measured current is outside, i.e. outside, the normal (expected) range, the external audio processor device is switched back from temporarily ON mode to the power saving OFF mode/sleep mode ((as indicated by follow up $T_2$ period). Alternatively, if the measured current is within the normal (expected) range, the external audio processor device remains in the ON mode (or is switched to permanent ON mode).

Figure 2B:
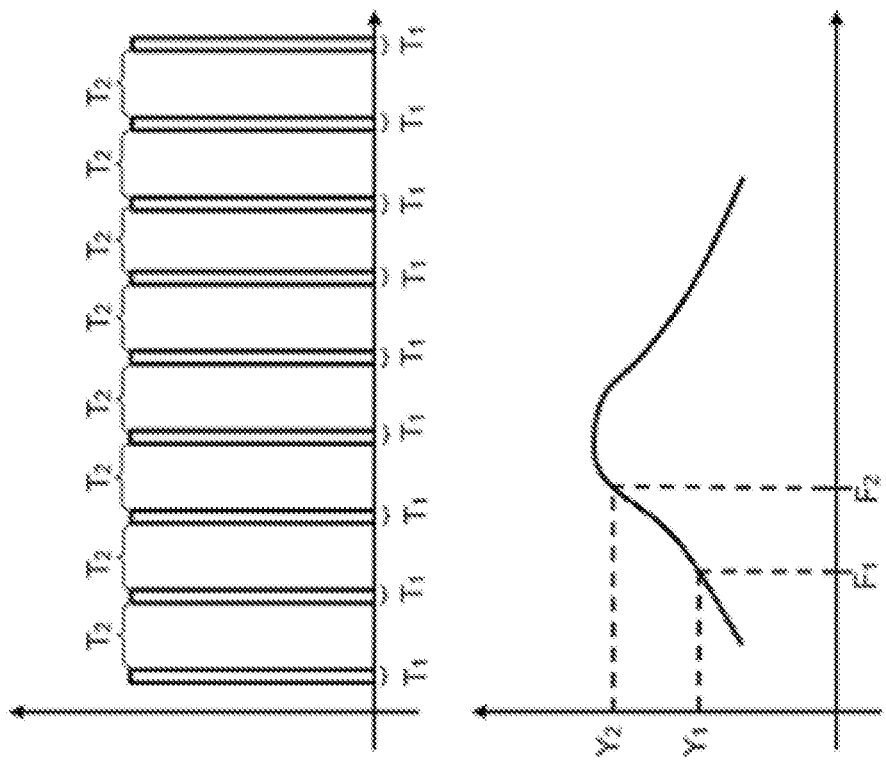
FIG. 2B shows a second graph with two alternating phases.

FIG. 2B illustrates a second curve showing the activity of the external audio processor device of a hearing device according to an aspect of the disclosure. The curve basically corresponds to the one shown in FIG. 2A except that the initial state of the hearing device is shown as an OFF/SLEEP mode. Also, the OFF mode/sleep mode time periods $T_2$, however, are significantly shorter than the ones shown in FIG. 2A. The temporarily ON mode time periods $T_1$ are also significantly shorter than the one shown in FIG. 2A.

Figure 2C:
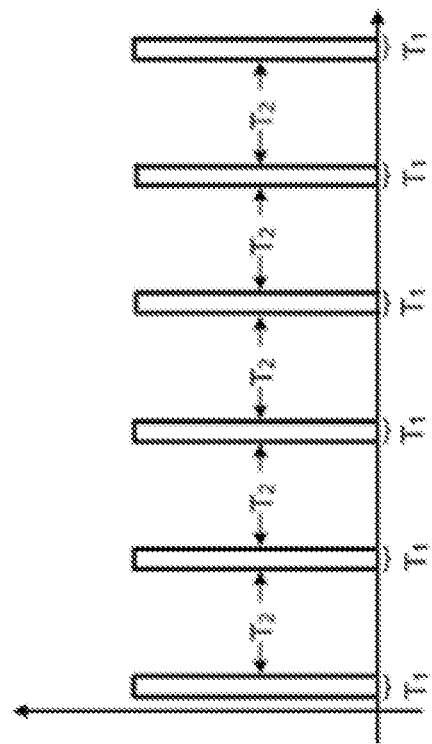
FIG. 2C shows a third graph with two alternating phases.

FIG. 2C illustrates a third curve showing the activity of the external audio processor device of a hearing device according to an aspect of the disclosure. The curve basically corresponds to the one shown in FIG. 2B, however, the OFF mode/sleep mode time periods $T_2$ are shorter than the ones shown in FIG. 3A and longer than the ones shown in FIG. 2B. The temporarily ON mode time periods $T_1$ are shorter than the one shown in FIG. 2A and longer than the ones shown in FIG. 2B.

As seen in FIG. 2A, FIG. 2B and FIG. 2C, it is possible to select the OFF mode/sleep mode time periods $T_2$ and the temporarily ON mode time periods $T_1$ as desired.

Figure 2D:
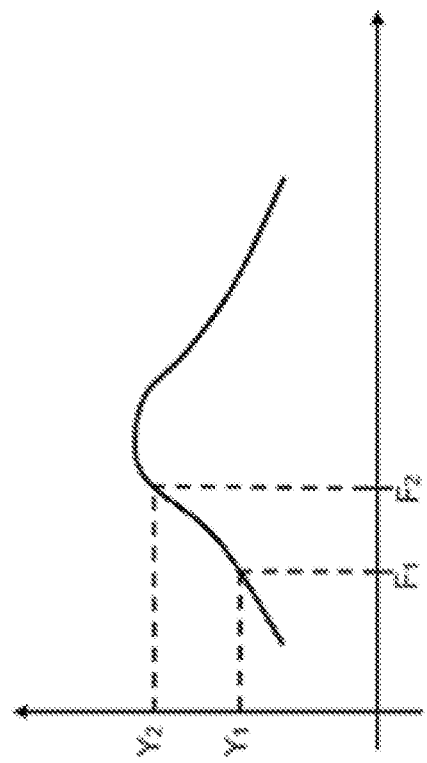
FIG. 2D shows a vibrator characteristic curve of a hearing device.

FIG. 2D illustrates a vibrator characteristic curve of a hearing device such as a bone conduction hearing aid. The signal force generated by a vibrator (generally electromagnetic) of a bone conduction hearing aid relates to alternating current (and voltage) applied to the coil of the vibrator. This alternating current (voltage) applied to the coil of the vibrator corresponds to the transmitter coil current/voltage across the transmitter coil, producing magnetic flux lines received by the receiver coil and eventually as alternating current by the coil of the vibrator.

The vibrator frequency curve shown in FIG. 2D, shows the force output of an implantable vibrator as a function of frequency. This frequency curve of the implantable vibrator, showing the force output as a function of frequency, represents frequency specific applied current to the vibrator coil and this in turn relates to characteristic transmitter coil current (or characteristic voltage across the transmitter coil). The characteristic transmitter coil current or characteristic voltage across the transmitter coil represent the characteristic parameter value. Thus, using a current measuring circuit (or alternatively a voltage measuring circuit) enables comparison of frequency specific transmitter current value (or alternatively voltage) across the transmitter coil during ON mode or OFF/SLEEP mode and the frequency specific characteristic current (or alternatively voltage).

In FIG. 2D a first frequency $F_1$ and a second frequency $F_2$ (that may represent one or more discrete tones) are indicated. Two vibration levels $Y_1$, $Y_2$ corresponding to the characteristic current (or alternatively voltage) at the first frequency $F_1$ and the second frequency $F_2$, respectively. The vibration levels $Y_1$ and $Y_2$ correspond to a specific characteristic transmitter current (or characteristic voltage value across the transmitter coil). Therefore, in one embodiment, performing the more than one discrete measurements and making a comparison with characteristic transmitter coil current value (or characteristic voltage value across the transmitter coil) for each frequency would allow to ascertain whether the measure quantity value (current or voltage) is an expected value (range) and accordingly the hearing device may be switched between different modes (ON or OFF/SLEEP). Thus, false positive for mode change may be avoided. In another embodiment, only one measurement and comparison is enough to determine whether the mode needs to be changed or not.

Figure 3B:
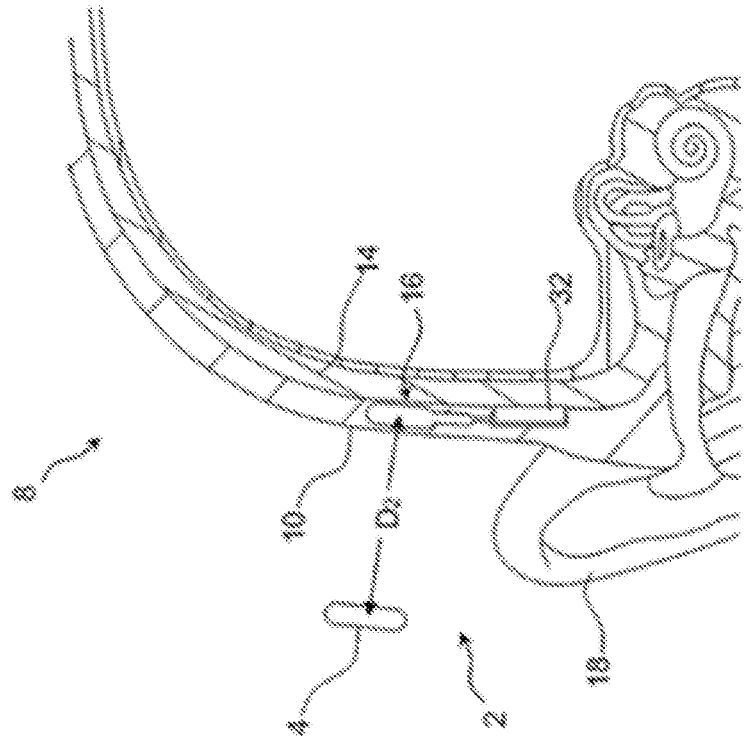
FIG. 3B shows the hearing device shown in FIG. 5A provided in a distance from the head of the hearing device user.
Figure 3A:
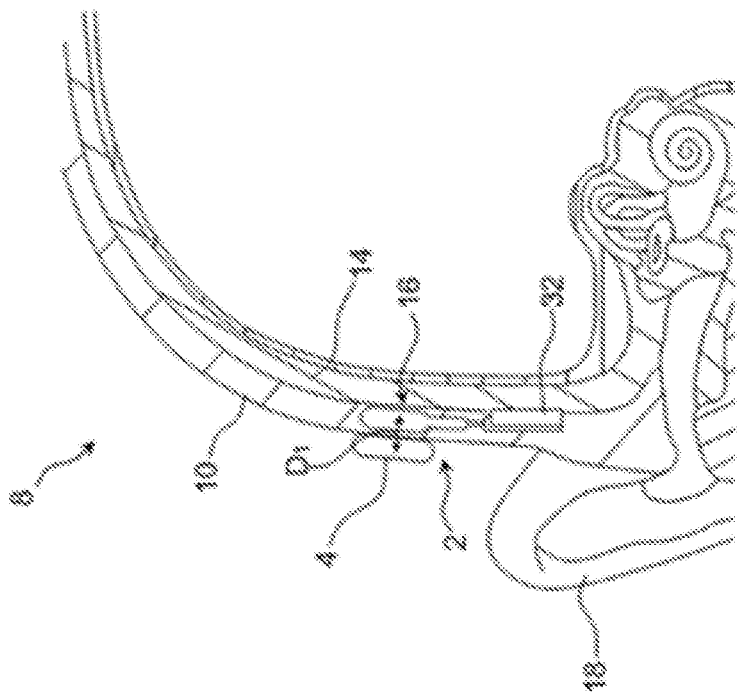
FIG. 3A shows a hearing device arranged on a hearing device user.

In the situation illustrated in FIG. 3A the distance $D_1$ between the coupling member 6 and the implantable prosthetic device 16 is as short as it can be since the external audio processor device 4 is attached to the skin 10 next to the ear 18 of the hearing device user 8.

FIG. 3B, however, shows the hearing device 2 shown in FIG. 3A provided in a distance from the head of the hearing device user 8. The distance $D_2$ between the coupling member 6 and the implantable prosthetic device 16 is larger than the distance $D_1$ in FIG. 5A.

The hearing device 2 is equipped with a detection device (not shown) configured to determine if the external audio processor device 4 is within a predefined distance from the implantable prosthetic system 16 or to determine if a coupling coefficient between the transmitter coil (not shown) of the coupling member 6 and a receiver coil (not shown) of the implantable prosthetic system 16 is within a predefined value range.

Accordingly, if the distance $D_2$ exceeds a certain value the hearing device 2 automatically detects that the distance $D_2$ exceeds this value and switches the hearing device 2 from the ON mode to the SLEEP mode/OFF mode, if the hearing device 2 is in the ON mode. On the other hand, if the hearing device 2 already is in the SLEEP mode/OFF mode, it will be remained in the SLEEP mode/OFF mode.

If the hearing device is in the SLEEP mode/OFF mode and the distance $D_2$ does not exceeds this value, the hearing device 2 automatically detects that the distance $D_2$ does not exceeds this value and switches the hearing device 2 from the SLEEP mode/OFF mode to the ON mode.

Figure 4:
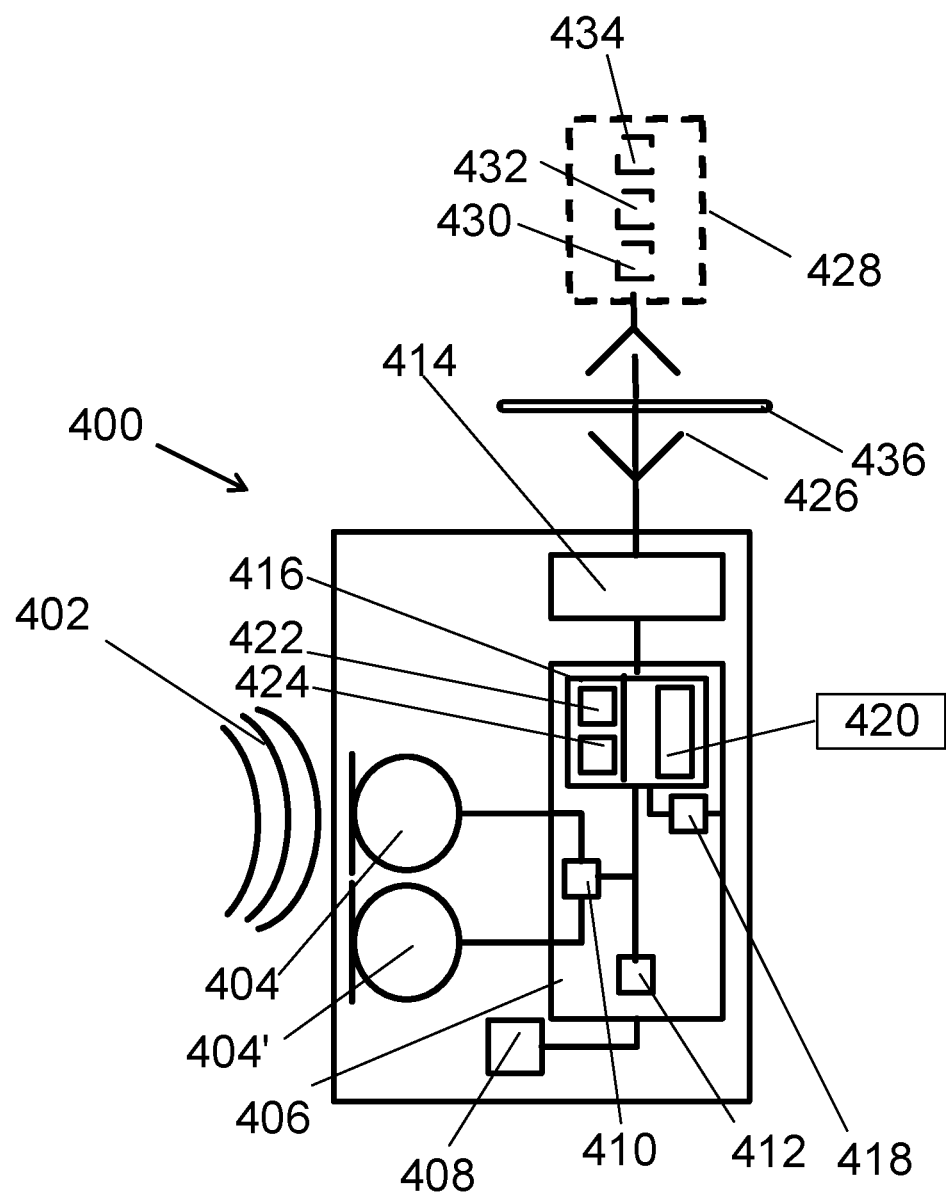
FIG. 4 shows an illustration of the bone conduction hearing device.

FIG. 4 shows an illustration of the bone conduction hearing device 400. The device 400 is adapted for processing signals comprising audio in order to assist a hearing impaired user. The hearing aid device 10 comprises a first microphone 404, and preferably additional microphones such as a second microphone 404'. The microphones are adapted to capture sound 402 from the surrounding and to covert it into an electrical signal.

The hearing device further includes an electrical circuitry 406 that comprises different functional units for example processing unit 412, analog-to-digital converter 410, memory 418, detection unit 416 and determination unit 420. The electrical signal comprising audio 402 are usually provided to an analog-digital-converter 410, which digitizes the signal to generate a digitized signal. The digitized signal is provided to the signal processing unit 412. The signal processing unit 412 is adapted to process the digitized signals to generate a processed signal in accordance with the needs of the hearing impaired user 48. The signal processing unit may include a filter bank in order to filter the incoming digitized signal in different frequency bands and process the bands by applying frequency specific amplification or other processing algorithms, which may include noise reduction, spatial directionality selection, sound source localization, gain reduction/enhancement, frequency filtering, and/or other processing operations common for hearing aids. The processed signal is transmitter using a transmitter 414 and an inductive link 426 across the skin 436 of the user. The power supply 408 provides energy for the operation of the external part and the implantable part of the hearing aid device. The signal processor 412 is adapted to modulate the processed signal in such a way that both data containing audio information and power may be transmitted transcutaneously across the skin.

The implantable part 428 comprises a receiver unit 430 that is adapted to receive the transmitted processed signal. The received signal is demodulated in a data signal and power signal at a demodulator 432. The power signal is used to supply energy to the implanted components including a vibrator 434, which utilizes the data signal to produce frequency specific vibrations to a bone such as a skull bone. The vibrations are transmitted via the skull bone to cochlea, thus generating sound perception to the hearing aid user.

The external part of the hearing aid device further comprises a detection unit 416, which may include at least one of the current measuring circuit 422 and voltage measuring circuit 424. Furthermore, the hearing aid includes a determination unit 420 and may also include a memory 418. The functioning of these components are in accordance with the description provided earlier in different combinable embodiments of this application.

It is intended that the structural features of the devices described above, either in the detailed description and/or in the claims, may be combined with steps of the method, when appropriately substituted by a corresponding process.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein.

Various modifications to these aspects will be readily apparent to those skilled in the art, and the generic principles defined herein may be applied to other aspects.

The claims are are to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A hearing device comprising:
an implantable prosthetic system including a receiver coil and a vibrator;
a memory; and
an external audio processor device comprising
a microphone configured to transform a received sound into an electrical input signal,
a signal processor configured to process the electrical input signal into a processed electrical data signal,
a transmitter coil configured to inductively transmit data signals and/or power across a user's skin to the receiver coil, and
a detection device configured to detect if the transmitter coil is within a predefined distance from the receiver coil or to detect if a coupling coefficient between the transmitter coil and the receiver coil is within a predefined value range, the detection device being configured to measure a quantity value associated with the transmitter coil for determining the distance between the transmitter coil and the receiver coil or the coupling coefficient between the transmitter coil and the receiver coil, wherein the external audio processor device further comprises:
a determination unit configured to automatically switch operating modes of the transmitter coil and/or the external audio processor device
I) from a permanent ON mode to a SLEEP/OFF mode, or
II) from the SLEEP/OFF mode to the permanent ON mode in accordance with the determined distance or the determined coupling coefficient, and
wherein during SLEEP/OFF mode, the determination unit is configured to
deactivate transmission from the transmitter coil for a first predefined time period,
activate the transmitter coil for a second predefined time period following the first predefined time period, during which the operating mode is a temporarily ON mode and the detection device determines if the transmitter coil is within the predefined distance from the receiver coil or if the coupling coefficient between the transmitter coil and the receiver coil is within the predefined value range; and
wherein if the external audio processor device is within the predefined distance from the implantable prosthetic system or if the coupling coefficient between the transmitter coil and the receiver coil is within the predefined value range, then the determination unit is configured to automatically switch the transmitter coil and/or external audio processor device from temporarily ON mode to permanent ON mode, or if the transmitter coil is outside the predefined distance from the receiver coil or if the coupling coefficient between the transmitter coil and the receiver coil is outside the predefined value range, then the determination unit is configured to deactivate the transmitter coil and switch the transmitter coil and/or external audio processor device from temporarily ON mode to SLEEP/OFF mode, the detection device comprises a parameter measuring circuitry, which in response to a controlled signal of predefined characteristics applied to the transmitter coil is configured to measure the quantity value associated with the transmitter coil for determining the distance between the transmitter coil and the receiver coil or coupling coefficient between the transmitter coil and the receiver coil, the detection device, in order to detect if the transmitter coil is within the predefined distance from the receiver coil or to detect if a coupling coefficient between the transmitter coil and the receiver coil is within the predefined value range, is configured to:

I) access a characteristic quantity value stored in a memory and the characteristic quantity value being defined in accordance with frequency curve parameters of the vibrator of implantable prosthetic system;

II) compare the measured quantity value with the accessed characteristic quantity value;

III) generate a compared result based on the comparison, representing the determined distance or coupling coefficient between the transmitter coil and a receiver coil, and IV) determine if the compared result is within a predefined acceptable variation.

2. The hearing device according to claim 1, wherein the controlled signal is provided using a battery, which is housed in a housing of the external audio processor device.

3. The hearing device according to claim 1, wherein

I) the parameter measuring circuitry comprises current measuring circuitry, the controlled signal includes a current signal, the predefined characteristics include a current of predefined magnitude corresponding to a stimulation current level for a specific frequency for the user, and the measured quantity value is the transmitter coil current; or II) the parameter measuring circuitry comprises voltage measuring circuitry, the controlled signal includes a voltage, the predefined characteristics include a voltage generating a current of predefined magnitude corresponding to a stimulation current level for a specific frequency for the user, and the measured quantity value is a voltage across the transmitter coil.

4. The hearing device according to claim 1, wherein the detection device is further configured to instruct the determination unit to I) with the transmitter coil and/or external audio processor in SLEEP/OFF mode, automatically switch the transmitter coil and/or external audio processor from SLEEP/OFF mode to permanent ON mode if the compared result is within the predefined acceptable variation, or II) with the transmitter coil and/or external audio processor in SLEEP/OFF mode, maintain the transmitter coil and/or external audio processor in SLEEP/OFF mode if the compared result is outside the predefined acceptable variation; or III) with the transmitter coil and/or external audio processor in permanent ON mode, automatically switch the transmitter coil and/or external audio processor from permanent ON mode to SLEEP/OFF mode if the compared result is outside a predefined acceptable variation, or IV) with the transmitter coil and/or external audio processor in permanent ON mode, maintain the transmitter coil and/or external audio processor in permanent ON mode if the compared result is within a predefined acceptable variation.

5. The hearing device according to claim 4, wherein the predefined acceptable variation corresponds to the predefined distance or the predefined value range.

6. The hearing device according to claim 1, wherein during the permanent ON mode, the determination unit is configured to generate, during recurrent time periods, the measured quantity value and compared result for determining if the receiver coil is within the predefined distance from the transmitter coil or if the coupling coefficient between the transmitter coil and the receiver coil is within the predefined value range; and if the compared result is within the predefined acceptable variation, then the determination unit is configured to maintain the transmitter coil and/or the external audio processor device in the permanent ON mode, or if the compared result is outside the predefined acceptable variation, then the determination unit is configured to deactivate the transmitter coil and automatically switch the transmitter coil and/or the external audio processor device from permanent ON mode to the SLEEP/OFF mode.

7. The hearing device according to claim 1, wherein when the compared result based on the measured quantity value is within the predefined acceptable variation, the parameter measuring circuitry is configured to measure at least one subsequent quantity value associated with the transmitter coil in response to at least one subsequent controlled signal of at least one subsequent predefined characteristics applied to the transmitter coil.

8. The hearing device according to claim 7, wherein the detection device is further configured to access at least one subsequent characteristic quantity value stored in the memory, the at least one subsequent characteristic quantity value being defined in accordance with the frequency curve parameters of the vibrator of the implantable prosthetic system; and generate at least one subsequent compared result by comparing the at least one subsequent measured quantity value with the at least one accessed subsequent characteristic quantity value.

9. The hearing device according to claim 8, wherein the determination unit is further configured to automatically switch the transmitter coil and/or external audio processor from SLEEP/OFF mode to permanent ON mode if the compared result and at least one subsequent compared result is within the predefined acceptable variation and at least one subsequent predefined acceptable variation respectively.

10. The hearing device according to claim 7, wherein the controlled signal and the at least one subsequent controlled signal comprise one or more discrete tones at a predefined modulation or a frequency sweep.

11. A hearing device comprising:

an implantable prosthetic system including a receiver coil and a vibrator;

an external audio processor;

a transmitter coil configured to inductively transmit data signals and/or power across a user's skin to the receiver coil;

a detection device configured to detect if the transmitter coil is within a predefined distance from the receiver coil or to detect if a coupling coefficient between the transmitter coil and the receiver coil is within a predefined value range, the detection device being configured to measure a quantity value associated with the transmitter coil for determining the distance between the transmitter coil and the receiver coil or the coupling coefficient between the transmitter coil and the receiver coil; and a determination unit configured to, based on the determined distance or the determined coupling coefficient, switch operating modes of the transmitter coil and/or the external audio processor device between:

I) a permanent ON mode,
II) a temporarily ON mode, or
III) a SLEEP/OFF mode, wherein during the SLEEP/OFF mode, the determination unit is configured to:
  deactivate transmission from the transmitter coil for a first predefined time period;
  activate the transmitter coil for a second predefined time period following the first predefined time period, during which the operating mode is the temporarily ON mode and the detection device determines if the transmitter coil is within the predefined distance from the receiver coil or if the coupling coefficient between the transmitter coil and the receiver coil is within the predefined value range for switching modes to the permanent ON mode or the SLEEP/OFF mode; and wherein the detection device is configured to, in order to detect if the transmitter coil is within the predefined distance from the receiver coil or to detect if a coupling coefficient between the transmitter coil and the receiver coil is within the predefined value range:

I) access a characteristic quantity value defined in accordance with one or more frequency curve parameters of the vibrator;

II) generate a compared result based on a comparison of the measured quantity value with the characteristic quantity value, the compared result representing the determined distance or coupling coefficient between the transmitter coil and the receiver coil; and III) determine if the compared result is within a predefined acceptable variation.

12. The hearing device according to claim 11, wherein the detection device comprises a parameter measuring circuitry which, in response to a controlled signal of predefined characteristics applied to the transmitter coil, is configured to measure the quantity value associated with the transmitter coil for determining the distance between the transmitter coil and the receiver coil or coupling coefficient between the transmitter coil and the receiver coil.

* * * * *